United States Patent
Bernal-Vazquez et al.

(10) Patent No.: US 9,133,101 B2
(45) Date of Patent: Sep. 15, 2015

(54) PROCESSES FOR THE PREPARATION OF (R)-2-ACETAMIDO-N-BENZYL-3-METHOXYPROPIONAMIDE AND INTERMEDIATES THEREOF

(75) Inventors: Pablo Miguel Bernal-Vazquez, Toluca (MX); José Miguel Lazcano-Seres, Calimaya (MX); Yaneth Mariá-Antonieta Contreras-Martinez, Hidalgo (MX); Jorge Alberto Juárez-Lagunas, Mexico (MX); Donato Sánchez-Mereles, Toluca (MX); Juan Rolando Vázquez-Miranda, Tepeji Del Rio (MX); Armando Zambrano-Huerta, Toluca (MX)

(73) Assignee: Signa S.A. de C.V. (MX)

( * ) Notice: Subject to any disclaimer, the term of this patent is extended or adjusted under 35 U.S.C. 154(b) by 0 days.

(21) Appl. No.: 14/342,285

(22) PCT Filed: Aug. 29, 2012

(86) PCT No.: PCT/IB2012/001667
§ 371 (c)(1),
(2), (4) Date: Jun. 10, 2014

(87) PCT Pub. No.: WO2013/030654
PCT Pub. Date: Mar. 7, 2013

(65) Prior Publication Data
US 2015/0025274 A1  Jan. 22, 2015

Related U.S. Application Data

(60) Provisional application No. 61/528,605, filed on Aug. 29, 2011.

(51) Int. Cl.
C07C 237/06 (2006.01)
C07C 227/18 (2006.01)
C07C 231/02 (2006.01)
C07C 231/14 (2006.01)
C07C 231/12 (2006.01)

(52) U.S. Cl.
CPC ............ *C07C 231/14* (2013.01); *C07C 227/18* (2013.01); *C07C 231/02* (2013.01); *C07C 231/12* (2013.01); *C07C 237/06* (2013.01)

(58) Field of Classification Search
CPC .. C07C 231/02; C07C 231/12; C07C 231/14; C07C 237/06; C07C 227/18
USPC .......................................... 564/139, 157, 165
See application file for complete search history.

(56) References Cited

U.S. PATENT DOCUMENTS

| 5,773,475 | A |  | 6/1998 | Kohn |  |
|---|---|---|---|---|---|
| 6,048,899 | A | * | 4/2000 | Kohn et al. | 514/626 |
| 7,884,134 | B2 | * | 2/2011 | Riedner et al. | 514/616 |
| 8,093,426 | B2 | * | 1/2012 | Madhra et al. | 564/165 |
| 2008/0027137 | A1 |  | 1/2008 | Riedner et al. |  |
| 2009/0143472 | A1 |  | 6/2009 | Madhra et al. |  |
| 2009/0298947 | A1 |  | 12/2009 | Mundorfer et al. |  |

FOREIGN PATENT DOCUMENTS

| CN | 101591300 A |   | 12/2009 |
|---|---|---|---|
| JP | 2010-037206 | * | 2/2010 |
| WO | 2006037574 A1 |   | 4/2006 |
| WO | 2007/076306 A1 |   | 7/2007 |
| WO | 2011/039781 A1 |   | 4/2011 |
| WO | 2011/092559 A1 |   | 8/2011 |
| WO | 2011/092672 |   | 8/2011 |
| WO | 2011/095110 A1 |   | 8/2011 |
| WO | 2011/095995 A1 |   | 8/2011 |
| WO | 2011/099033 A1 |   | 8/2011 |
| WO | WO 2011/092672 | * | 8/2011 |
| WO | 2011/144983 A2 |   | 11/2011 |

OTHER PUBLICATIONS

Andurkar et al, Tetrahedron Assymetry, 1998, 3841-3854.*
Choi, Daeock et al.; J. Med. Chem. 1996, 39, 1907-1916.
Duo Mei et al., Synthetic Communications, "Improved Enantioselective Synthesis of Protected (3s,4s)-4-Amino-3,5-dihydroxypentanoic Acid (ADPA)", Mar. 2010, vol. 40, Issue 8, pp. 1099-1105, XP0055048797.
Hulme, Alison N., "A flexible and efficient synthesis of the pyrrolidine [alpha]-glycosidase unhibitor 1, 4-dideoxy-1, 4-imino-D-arabinitol (DAB-1)", J. Chem Soc., Perkin Trans. 1, Jan. 2000, 12:1, pp. 1837-1841.
International Search Report and Written Opinion for Application No. PCT/IB2012/001667 dated Jan. 16, 2013.
IP.com Journal 2009, 9(4A), 35, "Novel intermediate compounds and their use in preparation of Lacosamide", IP.com No. IPCOM000181080D.
IP.com Journal 2009, 9(9B), 68, "Lacosamide (CAS RN = 175481-36-4) Diffraction Pattern", IP.com No. IPCOM000187362D.
Andurkar, Shridhar V. et al., "Sunthesis and anticonvulsant activities of (R)-(0)-methylserine derivatives", Tetrahedron: Asymmetry 1998, vol. 9, N. 21, pp. 3841-3854.

* cited by examiner

*Primary Examiner* — Shailendra Kumar
(74) *Attorney, Agent, or Firm* — Lerner, David, Littenberg, Krumholz & Mentlik, LLP

(57) ABSTRACT

This invention relates to processes for the preparation of (R)-2-acetamido-N-benzyl-3-methoxypropionamide (I) and intermediates thereof. Formula (I).

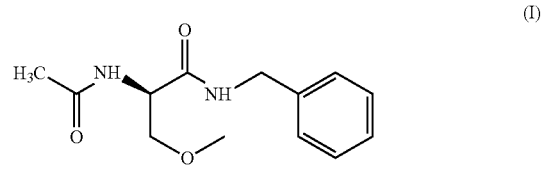

11 Claims, No Drawings

PROCESSES FOR THE PREPARATION OF (R)-2-ACETAMIDO-N-BENZYL-3-METHOXYPROPIONAMIDE AND INTERMEDIATES THEREOF

CROSS-REFERENCE TO RELATED APPLICATIONS

The present application is a national phase entry under 35 U.S.C. §371 of International Application No. PCT/IB2012/001667 filed Aug. 29, 2012, published in English, which claims priority from U.S. Provisional Application 61/528,605 filed Aug. 29, 2011, all of which are hereby incorporated herein by reference.

TECHNICAL FIELD

The present invention relates to the field of chemical synthesis of organic compounds and in particular to the synthesis of (R)-2-acetamido-N-benzyl-3-methoxypropionamide and intermediates thereof.

BACKGROUND (R)-2-Acetamido-N-benzyl-3-methoxypropionamide (I) belongs to a class of protected amino acids known to be useful for the treatment of partial-onset seizures in patients with epilepsy aged 17 years and older. It has been marketed in the United States under the trade name Vimpat®.

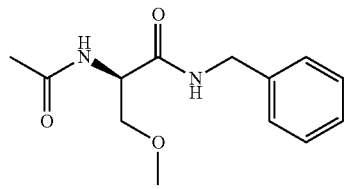

(1)

U.S. Pat. No. 5,773,475 discloses different processes to the preparation of anticonvulsant enantiomeric amino acid derivatives and pharmaceutical compounds thereof, and their use in treating CNS disorders in animals. A general method for the synthesis of aromatic compound N-benzyl-2-acetamido-3-methoxypropionamide is also disclosed.

US2008/027137 discloses a synthetic scheme for Lacosamide.

US2009/143472 discloses intermediates and their use in preparation of Lacosamide [(R)-2-(acetylamino)-N-benzyl-3-methoxypropionamide], its enantiomer and racemate.

CN 101591300 discloses a process for preparation of Lacosamide from N-Boc-D-serine or N-Cbz-D-serine.

US 20090298947 discloses different crystalline and amorphous forms of Lacosamide and processes to prepare them, pharmaceutical compounds containing the same, therapeutic uses thereof, and methods of treatment employing the same.

WO 2011/039781 discloses intermediates and their use in the preparation of Lacosamide [(R)-2-(acetylamino)-N-benzyl-3-methoxypropionamide].

WO 2011/039781 discloses intermediates and their use in the preparation of Lacosamide [(R)-2-(acetylamino)-N-benzyl-3-methoxypropionamide].

WO 2011/092559 discloses a process for the synthesis of Lacosamide using DL-serine as starting material, in which methylation reaction of hydroxyl is carried out using a base such as NaOH and an alkylating agent, such as Me p-toluenesulfonate. The R enantiomer is isolated from the racemic mixture of Lacosamide after selective hydrolysis of the acetamide, salification of the racemic mixture with a chiral acid in an organic solvent, resolution of the diastereoisomeric mixture, and subsequent acetylation of the optically pure intermediate.

WO 2011/092672 discloses different process for minimizing or removing impurities such as (2R)-2-(acetylamino)-3-(benzylamino)-3-oxopropyl acetate or (2R)-2-(propanoylamino-N-benzyl-3-methoxypropionamide in Lacosamide.

WO 2011/095110 discloses a process for the preparation of Lacosamide, and intermediate compounds thereof. For example, (2R)-2-(ethoxycarbonylamino)-3-hydroxy-N-(phenylmethyl)-propanamide was reacted with Me2SO4 in ethyl acetate in the presence of tetrabutylammonium bromide and KOH for (2R)-2-(ethoxycarbonylamino)-3-methoxy-N-(phenylmethyl)-propanamide. The intermediate obtained above was treated with HCl and then with NaOH to afford (2R)-2-amino-3-methoxy-N-(phenylmethyl)-propanamide, which was reacted with acetyl chloride in CH2Cl2 in the presence of triethylamine to give Lacosamide as the final product.

WO 2011/095995 discloses process for the preparation of Lacosamide [(R)-2-acetamido-N-benzyl-3-methoxypropanamide] from D-serine. The process utilizes high purity crystalline solids O-methyl-D-serine trifluoroacetate and N-acetyl-O-methyl-D-serine as key intermediates.

WO 2011/099033 discloses different processes for preparing and purifying (R)-2-acetamido-N-benzyl-3-methoxypropionamide and intermediates thereof.

Choi, Daeock et al. in *J. Med. Chem.* 1996, 39, 1907-1916 disclosed the synthesis and anticonvulsant activities of N-benzyl-2-acetamidopropionamide derivatives with six different heteroatom substituents (chloro, bromo, iodo, oxygen, nitrogen, and sulfur).

Andurkar, Shridhar V. et al., *Tetrahedron: Asymmetry* 1998, 9, 3841-3854 discloses procedures for the synthesis of (R)—N-benzyl-2-amino-3-methoxypropionamide, 2-acetamido-3-methoxypropionic acid, and O-methyl serine beginning from (R)—N-Cbz-serine.

*IP.com Journal* 2009, 9(4A), 35, describes the preparation of Lacosamide using phthaloyl.

*IP.com Journal* 2009, 9(98), 68 discloses a polymorphic form of Lacosamide which was obtained when a procedure from WO 2006037574 was followed.

SUMMARY

The present invention is directed to methods of preparation of an amino acid derivative, (R)-2-acetamido-N-benzyl-3-methoxypropionamide (I), various intermediates useful in the preparation of (R)-2-acetamido-N-benzyl-3-methoxypropionamide (I), and methods of preparation of intermediates therein.

In illustrative embodiments of the present invention, (R)-2-acetamido-N-benzyl-3-methoxypropionamide and the intermediates thereof may be prepared by an exemplary process as set out in Scheme 1. Exemplary reagents and conditions for these reactions are disclosed herein.

Scheme 1

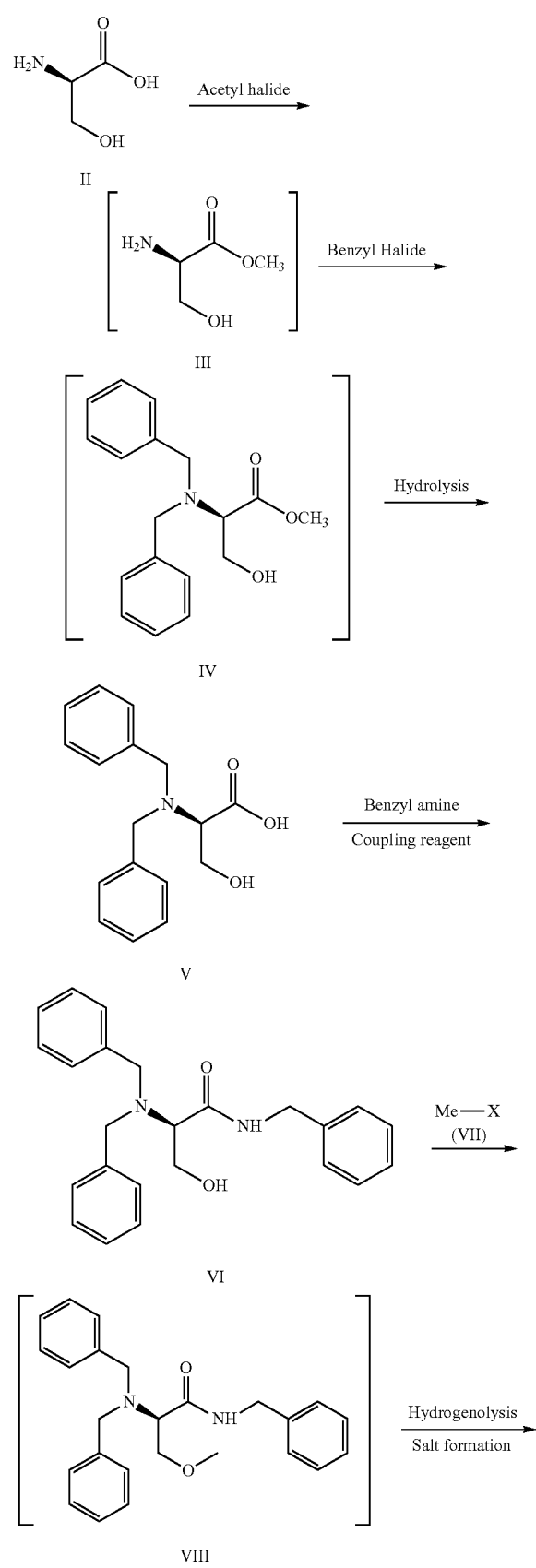

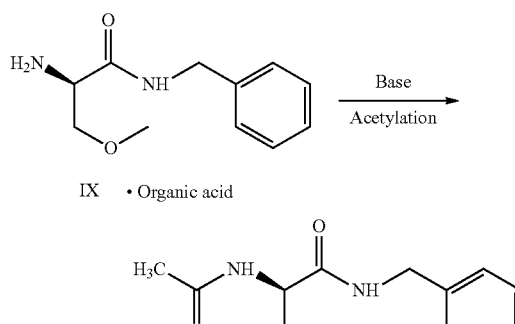

According to illustrative embodiments of the present invention, there is provided a process for the preparation of (R)-2-acetamido-N-benzyl-3-methoxypropionamide (I) comprising:

i. reacting, optionally in the presence of a first base and a phase-transfer catalyst, a compound of Formula VI:

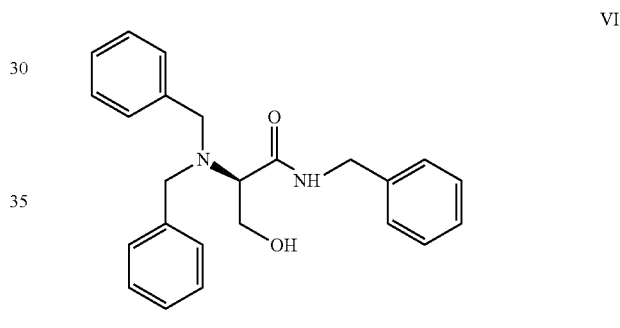

with a compound of Formula VII

Me-X      VII wherein Me-X is methylating agent such as a methyl halide (e.g. methyl iodide) or dimethyl sulfate, thereby forming a compound of Formula VIII:

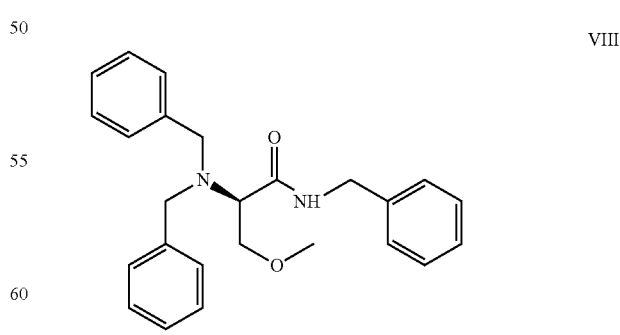

followed by catalytic hydrogenolysis in the presence of a suitable hydrogenolysis catalyst, followed by optional treatment with an organic acid, to produce an organic acid salt of a compound of Formula IX:

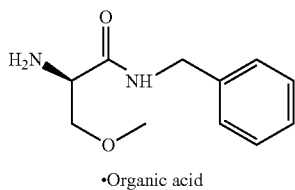

IX

• Organic acid ii. treating the organic acid salt of compound of Formula IX with a second base, followed by reaction, optionally in the presence of a third base, with an acylating reagent thereby forming (R)-2-acetamido-N-benzyl-3-methoxypropionamide (I):

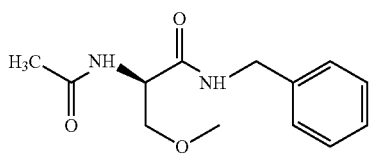

I

In illustrative embodiments of the present invention, there is provided a process for the preparation of a compound of Formula VI comprising:

i. forming a methyl ester using known methods, for instance reacting a compound of Formula II:

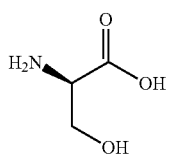

II with an acetyl halide in methanol to produce a methyl ester of a compound of Formula III:

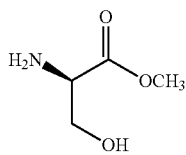

III wherein the acetyl halide is selected from the group consisting of an acetyl chloride, acetyl bromide and acetyl iodide; followed by reaction with benzyl halide, optionally in the presence of a fourth base, to produce a compound of Formula IV:

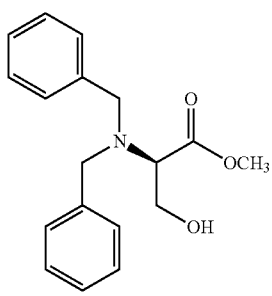

IV wherein the benzyl halide is selected from the group consisting of benzyl chloride, benzyl bromide and benzyl iodide;

followed by hydrolysis of the resulting compound in situ, in the presence of a fifth base to produce a compound of Formula V:

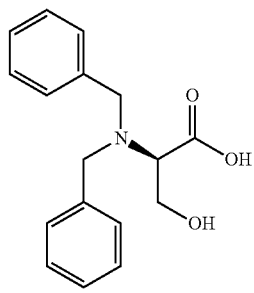

V ii. reacting, optionally in the presence of a sixth base, a carboxylic acid activating reagent to form an activated compound of Formula V which is reacted with benzyl amine to produce a compound of Formula VI:

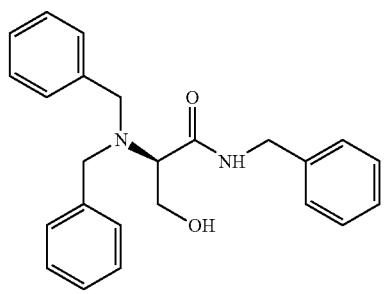

VI

In illustrative embodiments of the present invention, there is provided a compound of Formula VI:

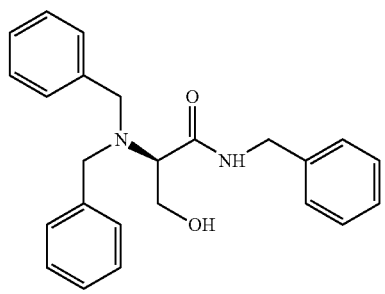

VI

In illustrative embodiments of the present invention, there is provided a compound of Formula VIII:

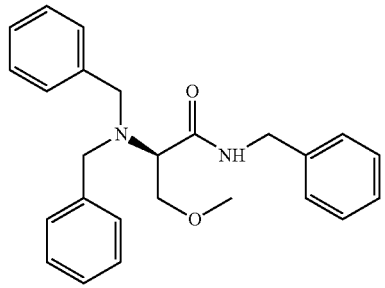

VIII

DETAILED DESCRIPTION

As used herein, the term pure means, unless otherwise stated, substantially free from impurities. Often compounds of the present invention are at least 75% pure (w/w), greater than about 90% pure (w/w), or greater than about 95% pure (w/w).

According to illustrative embodiments of the present invention, there is provided a process for the preparation of (R)-2-acetamido-N-benzyl-3-methoxypropionamide (I) comprising:

i. Reacting, optionally in the presence of a first base and a phase-transfer catalyst, a compound of Formula VI:

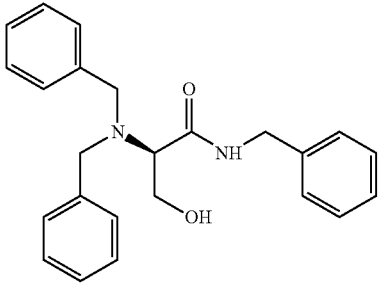

VI with a compound of Formula VII:

Me-X    VII wherein Me-X is methylating agent such as methyl iodide or dimethyl sulfate, thereby forming a compound of Formula VIII:

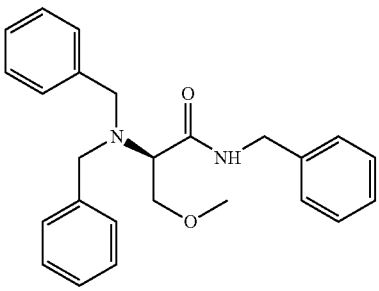

VIII followed by removal of the benzyl groups by catalytic hydrogenolysis in the presence of a suitable hydrogenolysis catalyst, followed by optional treatment with an organic acid, preferentially a chiral organic acid such as tartaric acid and derivatives such as dibenzoyltartaric acid, and mandelic acid and derivatives such as 2-chloromandelic acid, to form a compound of Formula IX:

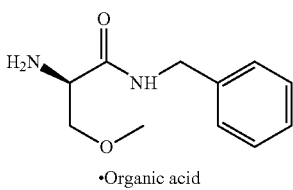

·Organic acid

IX ii. treating the compound of Formula IX with a second base, followed by reaction, optionally in the presence of a third base, with an acetylating reagent, thereby forming (R)-2-acetamido-N-benzyl-3-methoxpropionamide (I):

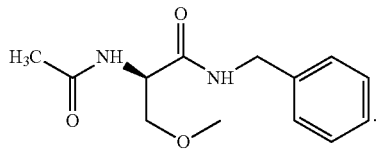

I

The first base may be inorganic or organic. The first base may be selected from the group consisting of metal hydroxides, carbonates, phosphates, tertiary amines, and aryl amines. The first base may be selected from the group consisting of: sodium hydroxide and potassium hydroxide. Other bases include lithium hydroxide, sodium carbonate, sodium bicarbonate, potassium carbonate, potassium bicarbonate, lithium carbonate, cesium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazanide (KHMDS), sodium hydride (NaH), potassium hydride (KH), potassium tert-butoxide, and mixtures thereof.

The reaction of the compound of Formula VI with the compound of Formula VII wherein X is a halogen or methylsulphate may be conducted in a first solvent. The first solvent may be a suitable aprotic organic solvent. The first solvent may be selected from the group consisting of alkyl ethers (e.g. tetrahydrofuran, dioxane, diethyl ether, methyl ethyl ether, methyl t-butyl ether, diisopropyl ether, butyl ether), aromatic and aliphatic hydrocarbons (e.g. benzene, toluene, xylenes, hexanes and heptanes), nitriles (e.g. acetonitrile, propionitrile, butyronitrile, and benzonitrile), sulfoxides and sulfones (e.g. dimethyl sulfoxide and sulfolane), halogenated hydrocarbons (e.g. dichloromethane and dichloroethane), and mixtures thereof.

The reaction of the compound of Formula VI with the compound of Formula VII wherein X is halogen or methylsulfate may be conducted optionally in the presence of a phase transfer catalyst selected from the group consisting of tetramethylammonium bromide, tetramethylammonium chloride, tetraethylammonium bromide, tetraethylammonium chloride, tetrabutylammonium bromide, tetrabutylammonium chloride, and tetrabutuylammonium iodide.

The N-debenzylation step may be conducted in a second solvent. The second solvent may be a suitable protic or aprotic organic solvent. The second solvent may be selected from the group consisting of alcohols (e.g. methanol, ethanol, propanol, isopropanol, butanol). Other suitable solvents include alkyl ethers (e.g. tetrahydrofuran, dioxane, diethyl ether, methyl t-butyl ether, diisopropyl ether, butyl ether), alkyl esters (e.g. ethyl acetate, isopropyl acetate), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), halogenated hydrocarbons (e.g. dichloromethane and dichloroethane), organic acids (e.g. formic acid and acetic acid) and mixtures thereof.

During the hydrogenolysis step, the benzyl groups on the amine nitrogen are selectively removed leaving the N-benzyl amide group intact. This allows subsequent selective acetylation of the amine nitrogen in the presence of the amide nitrogen.

The suitable hydrogenolysis catalyst may be selected from the group consisting of palladium, platinum, rhodium, ruthenium, and nickel. Often the hydrogenolysis catalyst is palladium on carbon, platinum on carbon or Raney-nickel. The catalyst loading may be from about 0.1 wt % to about 100 wt % palladium with respect to the weight of the compound of Formula VIII. The catalyst loading may be from about 0.1% to about 20% with respect to the weight of the compound of Formula VIII. The suitable hydrogenolysis catalyst may be finely dispersed solids or adsorbed on an inert support such as carbon or alumina. The suitable hydrogenolysis catalyst may be 5 wt % palladium on carbon. The hydrogenolysis may be performed by using hydrogen gas or transfer hydrogenolysis. A catalyst moistened with water, for instance 50% water wet 5% palladium on carbon is also suitable.

In an embodiment, preparation of the organic acid salt of the compound of Formula IX is a one-pot process whereby O-methylation of the compound of Formula VI with the methylating agent VII yields the compound of Formula VIII, which upon N-debenzylation and without isolation, and treatment with an organic acid, provides the organic acid salt of the compound of Formula IX directly. The organic acid used to form the salt may be preferentially selected from the group consisting of chiral organic acids such as tartaric acid and derivatives such as dibenzoyltartaric acid and mandelic acid and derivatives such as 2-chloromandelic acid.

In another embodiment, the organic acid salt of the compound of Formula IX is not formed, but rather a compound of Formula IX-A is formed by not treating with the organic acid. The remainder of the reaction to form (R)-2-acetamido-N-benzyl-3-methoxypropionamide (I) occurs in the same manner as if the organic acid salt of the compound of Formula IX had been formed.

Optionally, following the reaction of the compound of the Formula VI with the methylating agent (VII), an intermediate compound of Formula VIII may be isolated prior to catalytic hydrogenolysis.

The second base may be inorganic or organic. The second may be selected from the group consisting of metal hydroxides, carbonates, phosphates, tertiary amines, and aryl amines. The second base may be selected from the group consisting of aqueous sodium hydroxide, potassium hydroxide, lithium hydroxide, ammonium hydroxide, sodium carbonate, sodium bicarbonate, potassium carbonate, potassium bicarbonate, lithium carbonate, cesium carbonate, potassium hydrogen phosphate, sodium hydrogen phosphate, triethylamine, diisopropylamine, dimethylaminopyridine, pyridine, hexamethyldisilazide (HMDS), n-butyl lithium, lithium diisopropylamide (LDA), sodium hexamethyldisilazide (NaHMDS), potassium hexamethyldisilazide (KHMDS), sodium hydride (NaH), potassium hydride (KH), potassium tert-butoxide and mixtures thereof.

Treatment of the compound of Formula IX with a second base may be conducted in a third solvent. The third solvent may be a suitable protic or aprotic organic solvent. The third solvent may be selected from the group consisting of most preferably alcohols (e.g. methanol, ethanol, propanol, isopropanol, butanol) and water. Other solvents may include alkyl ethers (e.g. tetrahydrofuran, dioxane, diethyl ether, methyl ethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. benzene, toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethylsulfoxide and sulfolane), halogenated hydrocarbons (e.g. dichloromethane and dichloroethane), and mixtures thereof.

The suitable acylating agent may be selected from the group consisting of acetic anhydride, acetic acid or an acyl halide such as acetyl chloride, acetyl bromide or acetyl iodide.

The third base may be inorganic or organic. The third base may be selected from the group consisting of metal hydroxides, carbonates, phosphates, tertiary amines, and aryl amines. The third base may be selected from the group consisting of sodium carbonate, sodium bicarbonate, potassium carbonate, potassium bicarbonate, lithium carbonate, cesium carbonate, potassium phosphate, sodium phosphate, triethylamine, diisopropylamine, and mixtures thereof.

The reaction of the compound of Formula IX-A with an acylating reagent may be conducted in a fourth solvent. The fourth solvent may be a suitable aprotic organic solvent. The fourth solvent may be selected from the group consisting of alkyl ethers (e.g. tetrahydrofuran, dioxane, diethyl ether, methyl t-butyl ether, diisopropyl ether, butyl ether), N,N-dialkylamides (e.g. N,N-dimethylformamide, N,N-dimethylacetamide, and N-methyl-2-pyrrolidinone), sulfoxides and sulfones (e.g. dimethylsulfoxide and sulfolane), halogenated hydrocarbons (e.g. dichloromethane and dichloroethane), and mixtures thereof.

The reaction of the compound of Formula IX-A with an acylating reagent in the presence of a third base may be performed at an elevated temperature, from about 0° C. to about the boiling point of any used solvent.

In illustrative embodiments of the present invention, there is provided a process for the preparation of a compound of Formula VI comprising:

i. forming the methyl ester using know methods, for instance contacting a compound of Formula II:

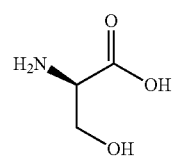

II with an acetyl halide in methanol to produce a methyl ester of Formula III:

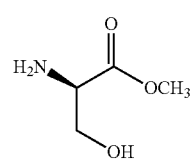

III wherein the acetyl halide is selected from the group consisting of acetyl chloride, acetyl bromide and acetyl iodide; followed by reaction with benzyl halide, optionally in the presence of a fourth base, to produce a compound of Formula IV:

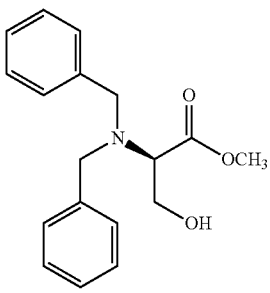

IV wherein the benzyl halide is selected from the group consisting of benzyl chloride, benzyl bromide and benzyl iodide; followed by hydrolysis of the resulting compound in situ, in the presence of a fifth base to produce a compound of Formula V:

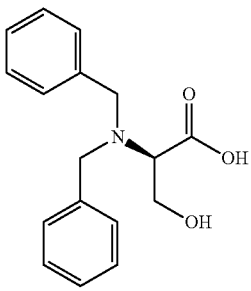

V ii. reacting, optionally in the presence of a sixth base, a carboxylic acid activating reagent to form an activated compound of Formula V which is reacted with benzyl amine to produce a compound of Formula VI:

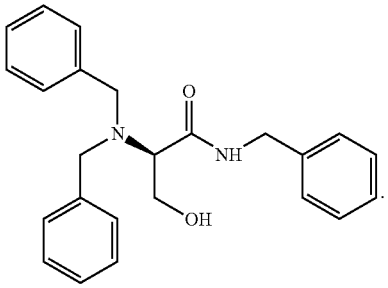

VI

The reaction of the compound of Formula II (D-serine) with an acetyl halide may be conducted in a fifth solvent. The fifth solvent may be a suitable aprotic organic solvent. An alcohol and optionally a co-solvent selected from the fifth solvent from the group consisting of alkyl ethers (e.g. tetrahydrofuran, dioxane, diethyl ether, methyl ethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic, and aliphatic hydrocarbons (e.g. benzene, toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

Optionally, following the reaction of the compound of Formula II with the acetylating agent, an intermediate methyl ester compound of a Formula III may be isolated prior to reaction with a benzyl halide.

The fourth base may be inorganic or organic. The fourth base may be selected from the group consisting of metal hydroxides, carbonates, phosphates, tertiary amines, and aryl amines. The fourth base may be selected from the group consisting of sodium hydroxide, potassium hydroxide, lithium hydroxide, sodium carbonate, sodium bicarbonate, potassium carbonate, potassium bicarbonate, lithium carbonate, cesium carbonate, potassium phosphate, sodium phosphate, triethylamine, diisopropylamine, N,N-dimethylaniline, N,N-diethylaniline, dimethylaminopyridine, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide and mixtures thereof.

The reaction of the compound of Formula III with benzyl halide may be conducted in a sixth solvent. The sixth solvent may be a suitable aprotic organic solvent. The sixth solvent may be selected from the group consisting of alcohols (e.g. methanol, ethanol, propanol, isopropanol, butanol), alkyl ethers (e.g. tetrahydrofuran, dioxane, diethyl ether, methyl ethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic, and aliphatic hydrocarbons (e.g. benzene, toluene, xylenes, hexanes, octanes and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethylsulfoxide and sulfolane), halogenated hydrocarbons (e.g. dichloromethane and dichloroethane), and mixtures thereof.

Optionally, following the reaction of the compound of Formula III with benzyl halide, an intermediate compound of Formula IV may be isolated prior to hydrolysis to a compound of Formula V.

The fifth base for hydrolysis may be inorganic or organic. The fifth base may be selected from the group consisting of metal hydroxides, for instance selected from the group consisting of sodium hydroxide, potassium hydroxide, lithium hydroxide, and mixtures thereof.

The hydrolysis of the compound of Formula IV in the presence of a fifth base may be conducted in a seventh solvent. The seventh solvent may be a suitable protic organic solvent. The seventh solvent may be preferably selected from the group consisting of water, alcohols (e.g. methanol, ethanol, propanol, isopropanol, butanol), and mixtures thereof.

In an embodiment, preparation of the compound of Formula V is a one-pot process whereby esterification of a compound of Formula II (D-Serine) with acetyl halide yields a compound of Formula III, which reacts, without isolation, with benzyl amine, to yield a compound of Formula IV, which upon hydrolysis, and without isolation, with a base, to generate the compound of Formula V.

The sixth base may be inorganic or organic. The sixth base may be selected from the group consisting of triethylamine, diisopropylamine, N,N-dimethylaniline, N,N-diethylaniline, dimethylaminopyridine, pyridine, and mixtures thereof.

The reaction of the compound of Formula V with benzyl amine may be conducted optionally in the presence of a peptide coupling reagent such as one selected from the group consisting of 1-hydroxy-benzotriazole, 1-hydroxy-7-aza-benztrazole, their salts or hydrates and mixtures thereof.

The reaction of the compound of Formula V with benzyl amine may be conducted optionally in the presence of a carbodiimide selected from the group consisting of N,N'-dicyclohexylcarbodiimide, N,N'-diisopropylcarbodiimide, 1-ethyl-3-(3-dimethylaminopropyl)carbodiimide or their salts and mixtures thereof.

The reaction of the compound of Formula V with benzyl amine may be conducted in an eighth solvent. The eighth solvent may be a suitable aprotic organic solvent. The eighth solvent may be selected from the group consisting of alkyl ethers (e.g. tetrahydrofuran, dioxane, diethyl ether, methyl ethyl ether, methyl t-butyl ether, diisopropyl ether, butyl ether), alkyl esters (e.g. ethyl acetate, isopropyl acetate), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethylsulfoxide and sulfolane), halogenated hydrocarbons (e.g. dichloromethane and dichloroethane), and mixtures thereof.

In illustrative embodiments of the present invention, (R)-2-acetamido-N-benzyl-3-methoxypropionamide (I) and the intermediates thereof may be prepared by an exemplary process as set out in Scheme 2. Exemplary reagents and conditions for these reactions are disclosed herein in examples.

Scheme 2

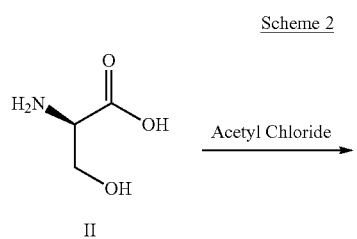

II

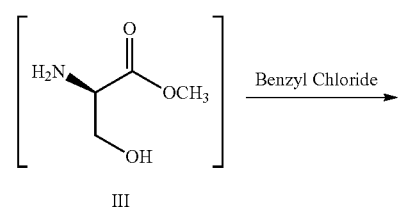

III

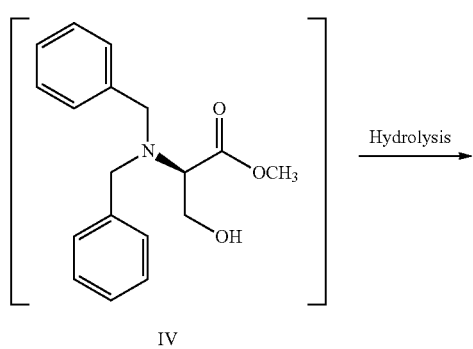

IV

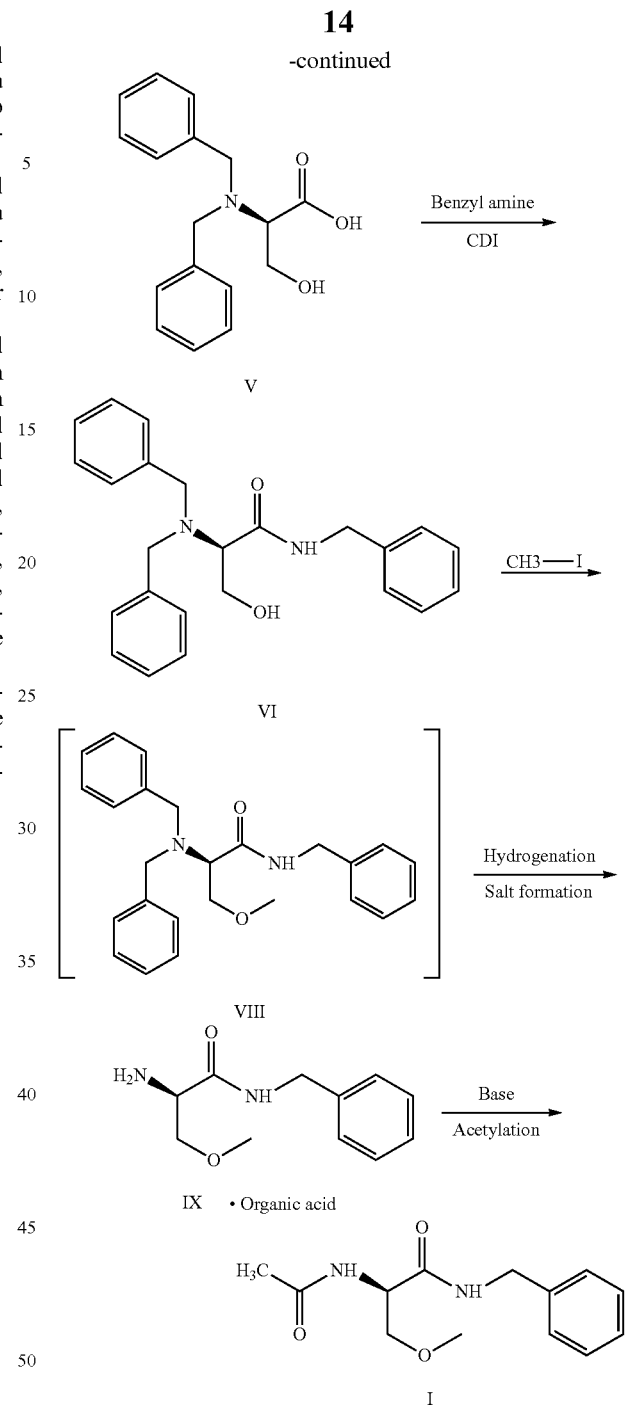

In illustrative embodiments of the present invention, there is provided a compound of Formula VI:

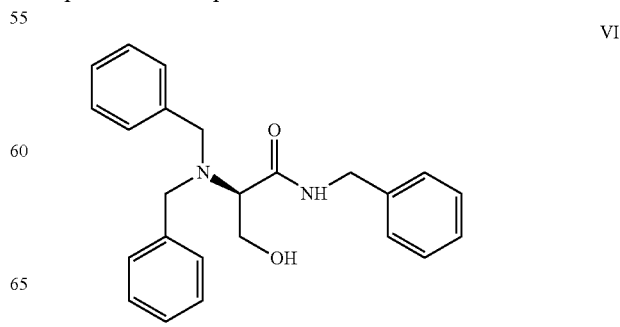

In illustrative embodiments of the present invention, there is provided a compound of Formula VIII:

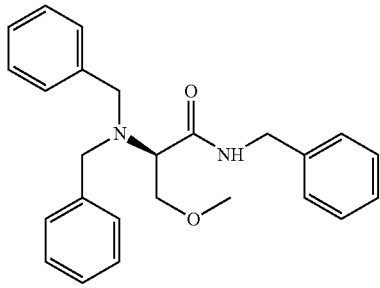

VIII

EXAMPLES

The following examples are illustrative of some of the embodiments of the invention described herein. These examples do not limit the spirit or scope of the invention in any way.

Example 1

Preparation of (R)-2-(dibenzylamino)-3-hydroxypropanoic acid

To the suspension of D-serine (105.09 g, 1.0 moL) in methanol (630 mL) was added acetyl chloride (117.75 g, 1.5 moL) slowly and under constant stirring over a 1 hour period at −5° C. The reaction mixture was heated to reflux and stirred for 24 hours. The reaction mixture was cooled at 0-5° C. and charged with sodium bicarbonate (298.20 g, 3.55 moL), sodium iodide (37.47 g, 0.25 moL) and benzyl chloride (259.50 g, 2.05 moL). The reaction mixture was heated to reflux and stirred for 12 hours. The reaction mixture was cooled to room temperature, filtered through a Celite® pad and the filter cake was washed with methanol (157 mL). The filtered methanolic solution was added dropwise, to a cooled solution of KOH (224.44 g 4.0 moL) in water (525 mL) at below 5° C. The reaction mixture was stirred 0-5° C. for 20 hours. Water (174 mL) was charged and the pH adjusted to 6.5 to 7.0 by dropwise addition of 30% HCl. The reaction mixture was heated to 20-25° C. and the pH was adjusted to 3.0 to 3.4 by dropwise addition of 30% HCl. The reaction mixture was stirred at 20-25° C. for 30 minutes, cooled to 15° C. and stirred for 30 min. The reaction mixture was filtered and the filter cake was washed three times with water (315 mL). The resulting solid was dried under vacuum at 45-50° C. for about 12 hours to provide (R)-2-(dibenzylamino)-3-hydroxypropanoic acid as a white solid (228.04 g, yield 80.0%, HPLC purity >99.6%).

$^1$H NMR (300 MHz, DMSO-d$_6$) δ 12.52 (1H, brs), 7.47-7.25 (10H, m), 4.76 (bs, 1H), 3.89-3.82 (2H, m), 3.71-67 (2H, m).

$^{13}$C NMR (75 MHz, DMSO-d$_6$) δ 172.5, 139.4, 129.3, 129.0, 128.6, 128.3, 127.6, 127.1, 62.9, 60.3, 54.8.

Example 2

Preparation of (R)—N-benzyl-2-(dibenzylamino)-3-hydroxypropanamide

To the suspension of (R)-2-(dibenzylamino)-3-hydroxypropanoic acid (285.34 g, 1.0 moL) in dichloromethane (2.86 L) was added HOBt (202.68 g, 1.50 moL), triethylamine (111.31 g, 1.1 moL), benzyl amine (117.86 g 1.1 moL) and EDC.HCl (230.04 g, 1.2 moL) at 0-5° C. under constant stirring. The reaction mixture was stirred at below 10° C. for 16 hours. When the reaction was considered complete, the agitation was stopped and the phases were allowed to separate. The organic phase was washed with water (856 mL), saturated sodium bicarbonate (2×713 mL), water (713 mL) and finally with a mixture of 2.85 mL of 30% HCl and 570 mL of water. The organic phase was concentrated under reduced pressure to a final volume of about 485 mL. MTBE (770 mL) was added and distilled again under reduced pressure to a final volume of about 485 mL. The reaction mixture was cooled to 20-25° C., and charged with heptanes (856 mL). The reaction mixture was heated to 28-32° C. and stirred for 1 hour, then cooled to 0-5° C. and stirred for 3 hours. The obtained mixture was filtered and the cake was washed with cold (0-5° C.) heptanes (285 mL). The resulting solid was dried under vacuum at 45-50° C. for 12 hours to provide (R)—N-benzyl-2-(dibenzylamino)-3-hydroxypropanamide as a white solid (353.82 g, yield 95%, HPLC purity >99.95%).

$^1$H NMR (300 MHz, CDCl$_3$) δ 7.65 (1H, brs), 7.31-7.16 (10H, m), 4.52 (1H, dd, J=5.6, 14.7), 4.38 (1H, dd, J=5.6, 14.7), 4.20-4.12 (1H, m), 4.06-4.01 (1H, m), 3.86 (2H, d, J=13.4), 3.54 (2H, d, J=13.4), 3.41-3.87 (1H, m).

$^{13}$C NMR (75 MHz, DMSO-d$_6$) δ 174.0, 138.5, 137.9, 129.0, 128.9, 128.8, 127.9, 127.8, 127.7, 62.1, 57.9, 55.0, 43.4.

Example 3

Preparation of (R)-2-amino-N-benzyl-3-methoxypropanamide (2R,3R)-dihydroxytartrate To a suspension of (R)—N-benzyl-2-(dibenzylamino)-3-hydroypropanamide (374.28 g, 1.0 moL) in toluene (3743 mL) was added tetrabutylammonium bromide (12.89 g, 0.04 moL), 50% NaOH (720 g, 9.0 moL) and methyl iodide (1277.46 g, 9.0 moL) at 0-5° C. under constant stirring. The reaction mixture was stirred at 7-10° C. for 24 hours. Water (750 mL) was added and the reaction mixture was stirred for 30 minutes. The agitation was stopped and the phases were allowed to separate, whereupon the pH of organic phase was adjusted to 6.5 to 7.0 by addition of 30% HCl. The organic phase was washed with water (2×750 mL) and distilled under reduced pressure to a final volume of about 750 mL. It was charged with isopropanol (2.5 L) and acetic acid (78.06 g, 1.3 moL). The reaction mixture was charged with 50% wet 5% Pd/C (71.7 g, 0.0168 moL) and stirred under a hydrogen atmosphere at 40 to 98 psi and at 40-45° C. The reaction mixture was cooled to 20-25° C. and filtered through a Celite® pad and washed with isopropanol (1.1 L). The filtrate was added to a solution of L-(+)-tartaric acid (150.0 g, 1.0 moL) in isopropanol (750 mL) slowly under stirring at 60-65° C. The reaction mixture was cooled to 10-15° C., filtered and washed with cold (0-5° C.) isopropanol (2×375 mL). The obtained solid was dried under vacuum at 45-50° C. until a LOD of NMT 12% was obtained, to provide (R)-2-amino-N-benzyl-3-methoxypropanamide (2R,3R)-dihydroxysuccinate as a white solid (239.89 g, yield 90%, HPLC purity up to 99.0%, HPLC enantiomeric purity up to 99.5%).

$^1$H NMR (300 MHz, D$_2$O/DMSO-d$_6$) δ 7.45-7.24 (5H, m), 4.45 (2H, s), 4.40 (1H, s), 4.33 (1H, s), 4.20 (1H, t, J=4.5), 4.51-4.35 (2H, m), 3.79 (1H, dd, J=4.2, 8.4 Hz), 3.77 (2H, d, J=4.5), 3.31 (3H, s).

$^{13}$C NMR (75 MHz, D$_2$O/DMSO-d$_6$) δ 170.6, 170.2, 138.0, 128.8, 127.6, 59.2, 52.6, 43.6, 23.2.

Example 4

Preparation of (R)-2-acetamido-N-benzyl-3-methoxypropanamide (Lacosamide)

A suspension of (R)-2-amino-N-benzyl-3-methoxypropanamide (2R,3R)-dihydroxysuccinate (358.34 g, 1.0 moL, 1.0 eq) in water (720 mL) was cooled to 0-5° C., and the pH adjusted to 10 to 10.5 by the addition of aqueous 28% NH$_4$OH at below 10° C. The reaction mixture was extracted with dichloromethane (2×720 mL and 1×360 mL). The organic phase was charged with 4-(dimethylamino)pyridine (3.66 g, 0.03 moL), followed by acetic anhydride (112.3 g, 1.1 moL) slowly under constant stirring at 10-15° C. The reaction mixture was stirred at 10-15° C. for 30 to 60 min. The reaction mixture was heated to 20-25° C. and stirred for 1 hour. The reaction mixture was charged with water (1254 mL) and sodium bicarbonate (109.21 g, 1.3 moL) and stirred for 1 hour. The phases were allowed to separate and the aqueous phase was extracted with dichloromethane (2×360 mL) and concentrated to a volume of about 720 mL, charged with ethyl acetate (2.9 L) and concentrated to a volume of about 720 mL. This operation is repeated until the KF is less than 0.5%. The reaction mixture was charged with ethyl acetate (2.9 L) and heated to 60-65° C. Charcoal (3% by weight) was charged and the reaction mixture was heated to reflux and stirred for one hour. The reaction mixture was cooled to 60° C., filtered and the solid was washed with hot (60° C.) ethyl acetate (360 mL). The filtrate was cooled to 45-50° C. and stirred there for at least 4 hours and then cooled at 0-5° C. at a rate of 10° C./hour. The suspension was stirred for at least 3 hours to 0-5° C. and filtered. The resulting solid was washed with ethyl acetate (2×180 mL) and dried under vacuum at below 50° C. until a LOD of NMT 0.5% was obtained, to provide (R)-2-acetamido-N-benzyl-3-methoxypropanamide as a white solid (186.3 g, 75%, HPLC purity=99.8%, HPLC enantiomeric purity=100%).

$^1$H NMR (300 MHz, CDCl$_3$) δ 7.38-7.25 (5H, m), 7.22-7.15 (1H, br m), 6.78-6.76 (1H, br m), 4.70-4.60 (1H, m), 4.51-4.35 (2H, m), 3.79 (1H, dd, J=4.2, 8.4 Hz), 3.49 (1H, dd, J=4.2, 8.4), 3.46 (3H, s), 1.96 (3H, s).

$^{13}$C NMR (75 MHz, CDCl$_3$) δ 177.9, 168.9, 139.1, 130.5, 129.3, 128.9, 74.4, 71.7, 65.9, 60.5, 54.5, 44.8, 39.5, 25.4.

Various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. The invention includes all embodiments and variations substantially as hereinbefore described.

What is claimed is:

1. A process for the preparation of (R)-2-acetamido-N-benzyl-3-methoxpropanamide (I) comprising:

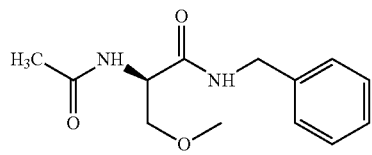

i. reacting, in the presence of a first base, a compound of Formula VI:

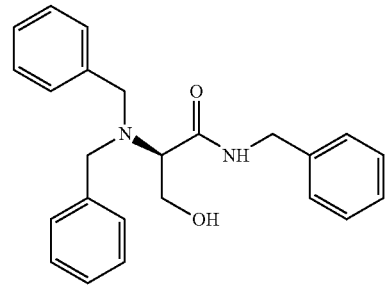

with a compound of Formula VII:

CH$_3$—X    VII wherein X is a halogen or methylsulfate, thereby forming a compound of Formula VIII:

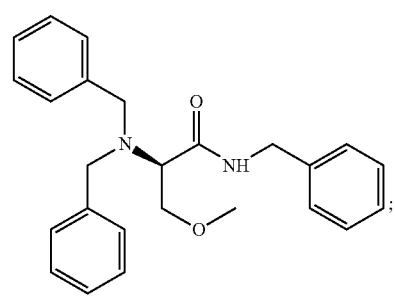

ii. hydrogenolysis, in the presence of a suitable hydrogenolysis catalyst, of the compound of the Formula VIII, thereby forming a compound of Formula IX-A:

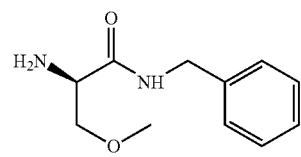

iii. treating the compound of Formula IX-A with a second base, followed by reaction with an acylating reagent, thereby forming (R)-2-acetamido-N-benzyl-3-methoxypropionamide (I):

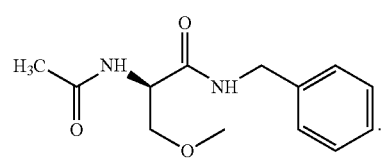

2. The process of claim 1 wherein the compound of Formula VIII is not isolated before hydrogenolysis.

3. The process of claim 1, wherein a phase-transfer catalyst is present in reacting the compound of Formula VI with the compound of Formula VII.

4. The process of claim 1 wherein an organic acid is used to treat the compound of Formula IX-A thereby forming an organic acid salt of Formula IX:

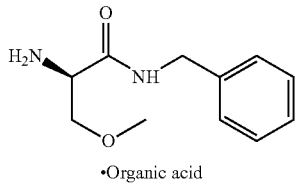

•Organic acid and then treating the compound of Formula IX-A with the second base followed by reaction with the acylating reagent in the presence of a third base.

5. The process of claim 1 wherein the reaction of the compound of Formula IX-A with the acylating agent is in the presence of a third base.

6. The process of claim 1 wherein the compound of Formula VIII is not isolated before hydrogenolysis, a phase-transfer catalyst is present in reacting the compound of Formula VI with the compound of Formula VII and an organic acid is used to treat the compound of Formula IX-A thereby forming an organic acid salt of a compound of Formula IX:

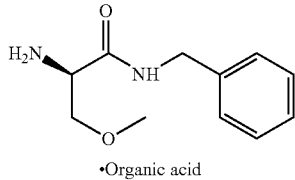

•Organic acid and then treating the compound of Formula IX-A with the second base followed by reaction with the acylating reagent in the presence of a third base.

7. A process for the preparation of the compound of Formula VI comprising:
   i. reacting a compound of Formula II:

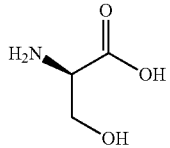

with an acetyl halide in the presence of methanol thereby forming a compound of Formula III:

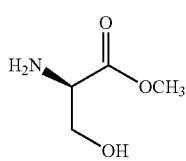

ii. N-benzylation of the compound of Formula III with benzyl halide, in the presence of a fourth base, thereby forming a compound of Formula IV:

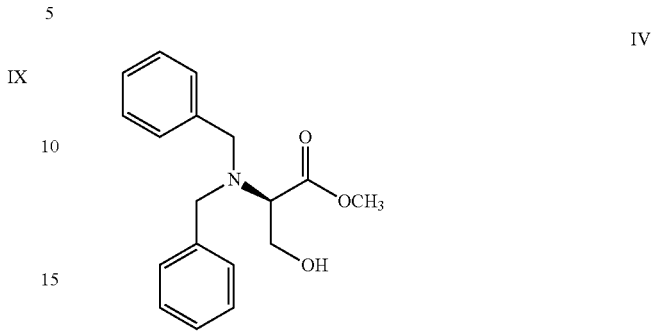

iii. hydrolysis of the compound of Formula IV, in the presence of a fifth base, thereby forming a compound of Formula V:

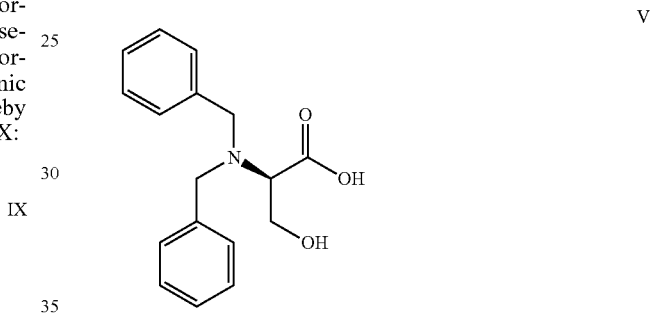

iv. reacting the compound of Formula V, in the presence of a sixth base, with a carboxylic acid activating reagent and benzyl amine, thereby forming a compound of Formula VI:

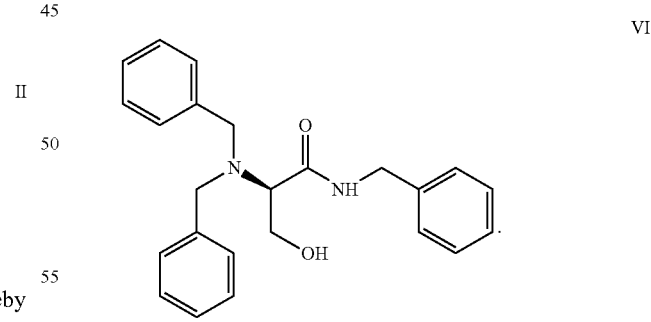

8. The process of claim 7 wherein the compound of Formula III is not isolated before N-benzylation of the compound of Formula III.

9. The process of claim 7 wherein the compound of Formula IV is not isolated before hydrolysis of the compound of Formula IV.

10. A compound of Formula VI:
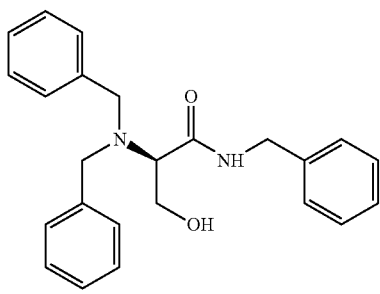
or a salt thereof.
11. A compound of Formula VIII:
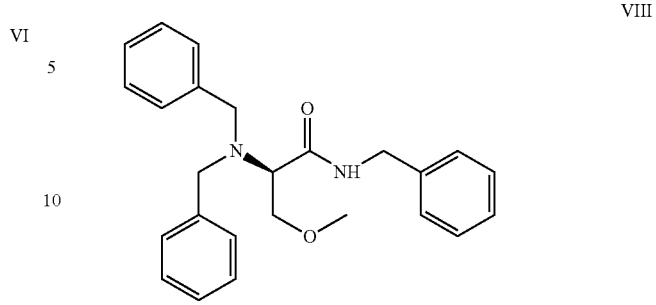
or a salt thereof.
* * * * *